United States Patent [19]

Dick et al.

[11] Patent Number: 5,614,551
[45] Date of Patent: Mar. 25, 1997

[54] INHIBITORS OF FATTY ACID SYNTHESIS AS ANTIMICROBIAL AGENTS

[75] Inventors: James D. Dick, Baltimore; Francis P. Kuhajda, Lutherville, both of Md.

[73] Assignee: The Johns Hopkins University, Baltimore, Md.

[21] Appl. No.: 188,421

[22] Filed: Jan. 24, 1994

[51] Int. Cl.$^6$ ............ A01N 43/20; A01N 25/26; A61K 31/335; A61K 9/127
[52] U.S. Cl. ............ 514/454; 514/558; 514/559; 514/560; 424/417; 424/450
[58] Field of Search ............ 514/12, 558, 559, 514/560, 454; 424/94.1, 248.52, 417, 450

[56] References Cited

U.S. PATENT DOCUMENTS

| | | | |
|---|---|---|---|
| 3,535,309 | 10/1970 | Hata et al. | 260/210 |
| 3,630,846 | 12/1971 | Hata et al. | 435/76 |
| 3,897,428 | 7/1975 | Omura et al. | 544/176 |
| 3,909,361 | 9/1975 | Hata et al. | 435/84 |
| 4,000,164 | 12/1976 | Parker | 549/479 |
| 4,011,334 | 3/1977 | Parker | 514/445 |
| 4,032,647 | 6/1977 | Parker | 514/445 |
| 4,110,351 | 8/1978 | Parker | 544/152 |
| 4,146,623 | 3/1979 | Parker | 424/248.52 |
| 4,328,246 | 5/1982 | Gold | 514/543 |
| 4,602,099 | 7/1986 | Parker | 549/579 |
| 4,738,984 | 4/1988 | Parker | 514/473 |
| 4,789,630 | 12/1988 | Bloch et al. | 435/5 |
| 4,877,782 | 10/1989 | Cazers et al. | 514/186 |
| 4,883,665 | 11/1989 | Miyazima et al. | 424/417 |
| 4,968,494 | 11/1990 | Claremon et al. | 424/94.64 |
| 5,070,009 | 12/1991 | Crepin | 435/6 |
| 5,110,731 | 5/1992 | Fisher | 431/119 |
| 5,143,907 | 9/1992 | Spielvogel | 514/64 |
| 5,185,149 | 2/1993 | Baldwin et al. | 424/94.63 |
| 5,188,830 | 2/1993 | Atkinson et al. | 424/94.63 |
| 5,190,969 | 3/1993 | Blumenstein et al. | 514/422 |
| 5,539,132 | 7/1996 | Royer et al. | 549/545 |

FOREIGN PATENT DOCUMENTS

| | | |
|---|---|---|
| 0246734 | 11/1987 | European Pat. Off. . |
| 0374886 | 6/1990 | European Pat. Off. . |
| 252616 | 12/1987 | Germany . |
| 59/225115 | 12/1984 | Japan . |
| 60/058917 | 4/1985 | Japan . |
| 1/132542 | 5/1989 | Japan . |
| 2/113850 | 4/1990 | Japan . |
| 2/247125 | 10/1990 | Japan . |
| WO93/12240 | 6/1993 | WIPO . |
| WO93/12756 | 7/1993 | WIPO . |

OTHER PUBLICATIONS

Bacchi, et al., "Effects of Some Antitumor Agents on Growth and Glycolytic Enzymes of the Flagellate *Crithidia*," *J. Bacteriol.*, 98:23–28 (1969).

Furnica, et al., "Mecanismes Biochimiques Impliques Dans La Sensibilisation Des Organismes Vivants Par Des Agents Chimiques A L'Action Des Radiations et Des Cytostatiques," *Rev. Roum. Biochim.*, 8:117–122 (1971).

Ōmura, et al., "Relationship Between the Structures of Fatty Acid Amide Derivatives and Their Antimicrobial Activities," *Antimicrobial Agents and Chemotherapy*, 6:207–215 (1974).

Ōmura, Satoshi, "The Antibiotic Cerulenin, a Novel Tool for Biochemistry as an Inhibitor of Fatty Acid Synthesis," *Bacteriological Reviews*, 40:681–697 (1976).

Altenbern, Robert A., "Cerulenin–Inhibited Cells of *Staphylococcus aureus* Resume Growth When Supplemented with Either a Saturated or an Unsaturated Fatty Acid," *Antimicrobial Agents and Chemotherapy*, 11:574–576 (1977).

Altenbern, Robert A., "Extreme Sensitivity of Staphylococcal Enterotoxin B and C Production in Inhibition by Cerulenin," *Antimicrobial Agents and Chemotherapy*, 11:906–908 (1977).

Partida, et al., "Comparative Effects of Diphenylglioxal and its Superoxide on Experimental Tumors," *Arch. de Farmacol. y Toxicol*, III:231–240 (1977).

Chen, et al., "The Cerulenin–Induced Formation of 1–Acyl–Lysophosphatidyl Glycerol in *Bacillus megaterium*," *Biochem. Biophys. Res. Comm.*, 80:126–132 (1978).

Carson, et al., "Effect of Cerulenin on *Streptococcus faecalis* Macromolecular Synthesis and Cell Division," *J. Bacteriol.*, 133:472–476 (1978).

Leung, et al., "*Streptococcus mutans* Dextransucrase: Effect of Cerulenin on Lipid Synthesis and Enzyme Production," *Infection and Immunity*, 28:846–852 (1980).

Smith, et al., "Thioesterase II, a New Marker Enzyme for Human Cells of Breast Epithelial Origin," *JNCI*, 73:323–329 (1981).

Carson, et al., "Effect of Cerulenin on Cellular Autolytic Activity and Lipid Metabolism During Inhibition of Protein Synthesis in *Streptococcus faecalis*," *J. Bacteriol.*, 146:590–604 (1981).

Bocquet–Pages, et al., "Lipid–Synthesis–Dependent Biosynthesis (or Assembly) of Major Outer–Membrane Proteins of *Escherichia oli*," *Eur. J. Biochem.*, 118:105–111 (1981).

Ōmura, Satoshi, Chapter 39 "Cerulenin" in *Methods in Enzymology*, 72:520–532 (1981).

Thompson, et al., "Purification and Properties Of Fatty Acid Synthetase From A Human Breast Cell Line," *Biochim. Biophys. Acta*, 662:125–130 (1981).

Ahmad, et al., "Studies on Acetyl–CoA Carboxylase and Fatty Acid Synthase from Rat Mammary Gland and Mammary Tumors," *Biochem. J.*, 208:443–452 (1982).

(List continued on next page.)

*Primary Examiner*—Keith D. Hendricks
*Assistant Examiner*—William W. Moore
*Attorney, Agent, or Firm*—Baker & Botts, L.L.P.

[57] ABSTRACT

Fatty acid synthase (FAS) is overexpressed by certain infectious organisms that are resistant to most currently available antibiotics. Contrarywise, little FAS expression is identified in patient tissues. Inhibition of fatty acid synthesis is thus selectively toxic to invasive cells, while patient cells with low FAS activity are resistant. This invention provides a method of treating septic patients where fatty acid synthesis by invading cells is inhibited with resultant interruption of the disease process.

14 Claims, No Drawings

OTHER PUBLICATIONS

Clements, et al., "Irreversible Inhibition of Fatty Acid Synthase from Rat Mammary Gland with S–(4–bromo–2,3–dioxobutyl)–CoA," *Biochem. J.*, 207:291–296 (1982).

Thompson, et al., "Lack of Coordinated Regulation Of Lipogenic Enzymes In A Human Breast Cell Line SKBr3," *Biochem. Biophys. Acta*, 712:217–220 (1982).

Mäntsälä, et al., "Secretion of β–lactamase by *Escherichia coli in vivo* and *in vitro:* Effect of Cerulenin," *Antonie van Leeuwenhoek*, 48:353–364 (1982).

Hayashi, et al., "Mechanism of Action of the Antibiotic Thiolactomycin Inhibition of Fatty Acid Synthesis of *Escherichia coli*," *Biochem. Biophys. Res. Comm.*, 115:1108–1113 (1983).

Spiegelman, et al., "Fibronectin Modulation of Cell Shape and Lipogenic Gene Expression in 3T2–Adipocytes," *Cell*, 35:657–666 (1983).

Mendoza, et al., "Thermal Regulation of Membrane Fluidity in *Escherichia coli*," *J. Biol. Chem.*, 258:2098–2101 (1983).

Mahajan, et al., "Cerulenin Inhibition of Lipid Synthesis and Its Reversal by Exogenous Fatty Acids in *Mycobacterium smegmatis* ATTC 607," *Can. J. Biochem. Cell Biol.*, 63:85–90 (1984).

Mahajan et al., "Cerulenin Effect on Phospholipid Metabolism in *Mycobacterium smegmatis* ATTC 607," *Biochim. Biophys. Acta*, 795:493–498 (1984).

Hait, et al., "Inhibition of Growth of Leukemic Cells by Inhibitors Of Calmodulin: Phenothiazines and Melittin," *Cancer Chemother. Pharmacol.*, 14:202–205 (1985).

Rainwater, et al., "Fatty Acid Biosynthesis in *Mycobacterium tuberculosis* var. *bovis Bacillus Calmette–Guerin*," *J. Biol. Chem.*, 260:616–623 (1985).

Abraham, et al., "Lipid Metabolism and Enzyme Activities In Hormone–Dependent and Hormone–Independent Mammary Adenocarcinoma in GR Mice," *JNCI*, 77:233–239 (1986).

Chalbos, et al., "Cloning of cDNA Sequences Of a Progestin–regulated mRNA from MCF7 Human Breast Cancer Cells," *Nucl. Acids Res.*, 14:965–981 (1986).

Pawlak, et al., "Evaluation of Thioesterase II as a Serum Marker for Rat Mammary Cancer," *Cancer Research*, 46:4712–4719 (1986).

Nishida, et al., "Effect of Thiolactomycin on the Individual Enzymes of the Fatty Acid Synthase System in *Escherichia coli*," *J. Biochem.*, 99:1447–1454 (1986).

Hoberg, et al., "Characterization of Cerulenin–Resistant Mutants of *Candida albicans*," *Infection and Immunity*, 51:102–109 (1986).

Tomada, et al., "Inhibition of acyl–CoA Synthetase by Triacsins," *Biochim. Biophys. Acta*, 921:595–598 (1987).

Chalbos, et al., "Fatty Acid Synthetase and Its mRNA Are Induced By Progestins in Breast Cancer Cells," *J. Biol. Chem.*, 262:9923–9926 (1987).

Debs, et al., "Selective Enhancement of Pentamidine Uptake in the Lung by Aerosolization and Delivery in Liposomes," *Amer. Rev. Respir. Dis.*, 135:731–737 (1987).

McAllister, et al., "The Effect of Tumour Growth on Liver Pantothenate, CoA, and Fatty Acid Synthetase Activity in the Mouse," *Br. J. Cancer*, 57:83–86 (1988).

Wilder, et al., "Altered Metabolic Rate and Fatty Acid Distribution in Adriamycin Resistant P388 Cells," *Proceedings of AACR*, 29–318, Abstr. 1265 (1988).

Tisdale, et al., "Changes in Host Liver Fatty Acid Synthase in Tumour–Bearing Mice," *Cancer Letters*, 42:231–235 (1988).

Bolla, et al., "The Assembly of the Major Outer Membrane Protein OmpF of *Escherichia coli* Depends on Lipid Synthesis," *The EMBO Journal*, 7:3595–3599 (1988).

Harris, et al., "Inhibition of Phenolic Glycolipid–1 Synthesis in Extracellular *Mycobacterium leprae* as an Indicator of Antimicrobial Activity," *International Journal of Leprosy*, 56:588–591 (1988).

Debs, et al., "Lung–Specific Delivery of Cytokines Induces Sustained Pulmonary and Systemic Immunomodulation in Rats," *J. Immunol.*, 140:3482–3488 (1988).

Spydevold, et al., "Activities of Enzymes of Lipid Metabolism in Morris Hepatoma," *Biochim. Biophys. Acta*, 1003:80–83 (1989).

Chambon, et al., "Progestins and Androgens Stimulate Lipid Accumulation In T47D Breast Cancer Cells Via Their Own Receptors," *J. Steroid Biochem.*, 33:915–922 (1989).

Wall et al., "Covalent Reaction of Cerulenin at the Active Site of acyl–CoA Reductase of *Photobacterium phosphoreum*," *Biochem. Cell Biol.*, 67:163–167 (1989).

Joyeux, et al., "Progestin Increases Gene Transcription and Messenger Ribonucleic Acid Stability of Fatty Acid Synthetase in Breast Cancer Cells," *Molecular Endocrinology*, 4:681–686 (1989).

Byers, et al., "Inhibition of *Vibrio harveyi* Bioluminescence by Cerulenin: *In Vivo* Evidence of Covalent Modification of the Reductase Enzyme Involved in Aldehyde Synthesis," *J. Bacteriol.*, 171:3866–3871 (1989).

Montgomery, et al., "Aerosolized Pentamidine as Second Line Therapy in Patients with AIDS and *Pneumocystis carinii* Pneumonia," *Chest*, 95:747–750 (1989).

Escot, et al., "Regulation of Fatty Acid Synthetase Ribonucleic Acid In The Human Endometrium During the Menstrual Cycle," *J. Clin. Endocrinol. Metab.*, 70:1319–1324 (1990).

Joyeux, et al., "Effects of Progestins and Menstrual Cycle on Fatty Acid Synthetase and Progesterone Receptor in Human Mammary Glands," *J. Clin. Endocrinol. Metab.*, 70:1438–1444 (1990).

Chalbos, et al., "Expression of the Progestin–Induced Fatty Acid Synthetase in Benign Mastopathies and Breast Cancer as Measured by RNA In Situ Hybridization," *JNCI*, 82:602–606 (1990).

Chalbos, et al., "Progestin–Induced Fatty Acid Synthetase in Breast Cancer," *Ann. N. Y. Acad. Sci.*, 595:67–73 (1990).

Hourdou, et al., "Specific Inhibition of Iturin Biosynthesis by Cerulenin," *Can. J. Microbiol.*, 36:164–168 (1990).

Amy, et al., "Molecular Cloning of the Mammalian Fatty Acid Synthase Gene and Identification of the Promoter Region," *Biochem. J.*, 271:675–679 (1990).

Ried, et al., "Role of Lipopolysaccharide in Assembly of *Escherichia coli* Outer Membrane Proteins OmpA, OmpC, and OmpF," *J. Bacteriol.*, 172:6048–6053 (1990).

Debs, et al., "Regulation of Gene Expression *in Vivo* by Liposome–mediated Delivery of a Purified Transcription Factor," *J. Biol. Chem.*, 265:10189–10192 (1990).

Chalbos, et al., "The Anti–progestin RU486 Stabilizes the Progestin–induced Fatty Acid Synthetase mRNA but Does Not Stimulate Its Transcription," *J. Biol. Chem.*, 266:8220–8224 (1991).

Tomada, et al., "Evidence for an Essential Role of Long Chain Acyl–CoA Synthetase in Animal Cell Proliferation," *J. Biol. Chem.*, 266:4214–4219 (1991).

Mathur, et al., "Molecular Cloning and Sequencing of the Gene for Mycocerosic Acid Synthase, a Novel Fatty Acid Elongating Multifunctional Enzyme, from *Mycobacterium tuberculosis* var. *bovis Bacillus Calmette–Guerin*," J. Biol. Chem., 267:19388–19395 (1992).

Weiss et al (1986) Biochem Hoppe–Seyler 367, 905–912.

Funabashi et al (1989) J. Biochem 105, 751–755.

Fujii et al (1986) Jpn. J. Exp. Med. 56, 99–106.

Kariya, T., and Wille, L.J., 1978, Biochemical and Biophysical Research Communications, 80(4):1022–1024.

Davidson, L.A., and Takayama, K., 1979, Antimicrobiol Agents and Chemotheraphy, 16(1): 104–105.

Halvorson, P.L., and MCune, S.A., 1984, Lipids, 19(11):851–856.

McCarthy, C. M., 1988, Current Microbiology, 17(2):121–125.

Barrow, W.W., et al., 1993, Antimicrobial Agents and Chemotherapy, 37(4):652–657.

Seyfzadeh, M., et al., 1993, Proceedings of the National Academy of Sciences, U.S.A., 90(23):11004–11008.

Rastogi, N., et al., 1994, Antimicrobial Agents and Chemotherapy, 38(10):2287–2295.

INHIBITORS OF FATTY ACID SYNTHESIS AS ANTIMICROBIAL AGENTS

U.S. Ser. No. 08/096,908, filed Jul. 26, 1993, and U.S. Ser. No. 07/917,716, filed Jul. 24, 1992, are incorporated herein in their entirety.

BACKGROUND OF THE INVENTION

1. Field of the Invention

This invention relates to the field of antibiotic and antiparasitic therapy. In particular this invention contemplates administration of inhibitors of fatty acid synthesis or metabolism to patients suffering from microbial or parasitic infection or colonization.

2. Background Information

In lower organisms such as yeast and bacteria fatty acid synthesis differs from that in humans. In bacteria (prokaryotes) the actual assembly of fatty acids occurs by seven separate enzymes. These enzymes are freely dissociable and are classified as Type II synthases. Type II fatty acid synthases are specifically inhibited by the drug Thiolactomycin. Thiolactomycin, (4S)(2E,5E)-2,4,6-trimethyl-3-hydroxy-2,5,7-cotatriene-4-thiolide, is a unique antibiotic structure that inhibits dissociated, but not multifunctional fatty acid synthases. The antibiotic is not toxic to mice and affords significant protection against urinary tract and intraperitoneal bacterial infections.

In higher organisms however, gene fusion events have occurred among the seven separate enzymes from bacteria. This resulted in multifunctional enzymes for fatty acid synthesis which are classified as Type I. In yeast, such as *S. cerevisiae*, there are two distinct polypeptides designated as alpha and beta which are responsible for fatty acid synthesis. The major products of fatty acid synthesis in yeast are 16 and 18 carbon saturated fatty acids produced as coenzyme-A derivatives. In mycobacterium, such as *M. smegmatis*, all of the enzyme activities are on one large polypeptide of 290,000 Da. The product of this synthase are 16 to 24 carbon saturated fatty acids derivatized to coenzyme-A. In pathogenic Mycobacterium, such as Nocardia species, there exists a second synthase, mycocerosic acid synthase (MAS). This synthase is responsible for very long chain branched fatty acids. Importantly, MAS contains a beta-ketoacyl synthetase (condensing enzyme) activity similar to that of Type I fatty acid synthases.

While Thiolactomycin is a specific inhibitor of Type II fatty acid synthases, cerulenin is a specific inhibitor of Type I fatty acid synthases. Cerulenin was originally isolated as a potential antifungal antibiotic from the culture broth of *Cephalosporium Caerulens*. Structurally cerulenin has been characterized as 2R,3S-epoxy-4-oxo-7, 10-trans, trans-dodecanoic acid amide. Its mechanism of action has been shown to be inhibition, through irreversible binding, of beta-ketoacyl synthase, the condensing enzyme required for biosynthesis of fatty acids. Cerulenin has been categorized as an antifungal, primarily against Candida and *Saccharomyces sp*. In addition, some in vitro activity has been shown against some bacteria, antinomycetes, and mycobacteria, although no activity was found against *Mycobacterium tuberculosis*. The activity of fatty acid synthesis inhibitors and Cerulenin in particular has not been evaluated against protozoa such as *Toxoplasma gondii* or other infectious eucaryotic pathogens such as *Pneumocystis carinii, Giardia lamblia, Plasmodium sp., Trichomonas baginalis, Crytosporidium, Trypanosoma, Leishmania*, and *Shistosoma*.

Despite cerulenin's in vitro activity against some bacteria and fungi it has not been developed as a therapeutic agent. To date research on this compound has centered on its use as a research tool for investigating the role of fatty acids in the metabolism and physiology of a variety of organisms because of its activity as a fatty acid synthesis inhibitor.

The rational for the use of fatty acid synthase inhibition as a topical and systemic therapy for various pathogens is based on the fact that the fatty acid biosynthetic pathway in man is normally down regulated due to the high fat content in our diet. In man, significant fatty acid synthesis may occur in two sites: the liver, where free palmitic acid is the predominant product (Roncari, *Can. J. Biochem.*, 52: 221–230, 1974); and lactating mammary glands where $C_{10}$–$C_{14}$ fatty acids predominate (Thompson, et al., *Pediatr. Res.*, 19: 139–143, 1985). Except for lactation, and cycling endometrium (Joyeux, et al., *J. Clin. Endocrinol. Metab.*, 70: 1319–1324, 1990), the fatty acid biosynthetic pathway is of minor physiologic importance, since exogenous dietary lipid intake down-regulates the pathway in the liver and other organs (Weiss, et at., *Biol. Chem. Hoppe-Seyler*, 367: 905–912, 1986).

Since fatty acid synthesis occurs at insignificant levels in humans but at high levels in various pathogenic microorganisms, the fatty acid biosynthetic pathway thus provides a potential selective target for the development of antibiotic and antiparasitic therapies.

SUMMARY OF THE INVENTION

It is an object of this invention to provide a method for treating infection in a mammal by administering a pharmaceutical composition that will selectively kill or inhibit the growth of the infecting microbe without substantially affecting normal mammalian metabolism.

It is another object of this invention to provide a method for treating infectious lesions of an externally accessible surface of an animal by non-invasive means.

In one embodiment, this invention provides a method of inhibiting growth in an animal of invasive microbial cells which are dependent on endogenously synthesized fatty acid, comprising administering an inhibitor of fatty acid synthesis to the animal in an amount sufficient to inhibit growth of the microbial cells.

In another embodiment, this invention provides a method of killing invading cells which are dependent on endogenously synthesized fatty acids, comprising administering to an animal invaded by the cells an inhibitor of fatty acid synthesis in an amount sufficient to inhibit synthesis of fatty acids by the invading cells, where the amount of inhibitor is insufficient to kill the animal.

In yet another embodiment, this invention provides a method of inhibiting growth of microbial cells in an infected animal comprising administering to the animal a pharmaceutical composition comprising an inhibitor of fatty acid synthesis, in a substantially non-systemic manner. In a preferred mode, the inhibitor of fatty acid synthesis is formulated in a pharmaceutical composition suitable for topical administration and administered locally for non-systemic therapy. In another preferred mode, the inhibitor of fatty acid synthesis is formulated in liposomes for administration as described above.

This invention describes the use of the inhibition of fatty acid biosynthesis as a means to treat various pathogenic or opportunistic organisms known to undergo endogenous fatty acid synthesis. The concentrations of an agent required to inhibit growth of these infectious agents in vitro indicate a potential therapeutic index in mammals, especially man. Moreover, some of these infectious agents, such as *M. tuberculosis* or *Candida species,* have Type I fatty synthases which are structurally similar but not identical to mammalian fatty acid synthase.

DETAILED DESCRIPTION OF THE INVENTION

I. Fatty Acid Synthesis in Lower Organisms

Fatty acid synthesis in bacteria or humans all require the following seven enzymatic functions (Wakil, S. J., *Biochemistry,* 28: 4523–4530, 1989):

acetyl transacylase malonyl transacylase beta-ketoacyl synthetase (condensing enzyme)

beta-ketoacyl reductase beta-hydroxyacyl dehydrase enoyl reductase thioesterase

Although bacteria and mammals share these enzyme activities they are organized differently phylogenetically. In bacteria, there are seven separate peptides, each peptide responsible for one enzymatic activity. This is classified as a Type II fatty acid synthase and is inhibited by the drug Thiolactomycin. In contrast, mycobacterium, yeast, and higher organisms have condensed these enzymatic activities to peptides with multiple enzymatic functions. For example, yeast have two separate polypeptides whereas in mycobacterium and mammals, all seven enzymatic activities are present on a single polypeptide. These are designated Type I fatty acid synthases.

Using standard in vitro growth inhibition assays, the inventors have demonstrated that inhibitors of Type I FAS, such as Cerulenin, reduce the growth of pathogenic mycobacterium, such as *M. tuberculosis,* including multiply drug resistant strains, and intracellular parasites, such as *Toxoplasma gondii.*

The concentration of cerulenin used to inhibit these organisms in vitro, is nontoxic toward normal human fibroblasts in culture. Indeed, *T. gondii* are intracellular parasites which are cultured within normal human fibroblasts. Cerulenin is able to kill the intracellular parasite without damaging the human fibroblasts. Thus, the endogenous fatty acid synthesis pathway is a selective target for the development of antibiotic therapy.

II. Antimicrobial Treatment Based on Inhibition of Fatty Acid Synthesis

The present invention provides a method for inhibiting growth of microbial cells that are dependent on endogenously synthesized fatty acid (i.e., fatty acid synthesized within the cells) without inhibiting metabolic activity of a mammal infected by the microbe. Infections or colonization may be reduced in such mammals by administering to the mammal one or more inhibitors that interfere with fatty acid synthesis or utilization. These inhibitors inhibit growth or are cytotoxic to microbial cells which undergo fatty acid synthesis, and administration which results in reduction of fatty acid synthesis and utilization by the microbial cells will reduce infection or colonization in the mammal.

A. Selection of the Patient Population

The method of this invention contemplates treatment of microbial cells that are dependent on endogenous fatty acid synthesis (i.e., fatty acid that is synthesized within the cell). Preferred patients may be identified because they are infected or are colonized by an organism known to depend upon endogenous fatty acid synthesis. These organisms may be identified by culture, antigen testing, direct nucleic acid hybridization techniques, such as PCR, or by microscopic identification of biopsies or fluids from the patient. In addition, patients may be identified, by in vitro susceptibility testing of organisms isolated from these patients using Type I FAS inhibitors or other inhibitors of fatty acid synthesis, excluding inhibitors of Type II fatty acid synthase. Infectious organisms that are susceptible to treatment with a fatty acid synthesis inhibitors include, *Mycobacterium tuberculosis,* especially multiply drug resistant strains, and protozoa such as *T. gondii.*

Infectious diseases which are particularly susceptible to treatment by the method of this invention are diseases which cause lesions in externally accessible surfaces of the infected animal. Externally accessible surfaces include all surfaces that may be reached by non-invasive means (without cutting or puncturing the skin), including the skin surface itself, mucus membranes, such as those covering nasal, oral, gastrointestinal, or urogenital surfaces, and pulmonary surfaces, such as the alveolar sacs. Susceptible diseases include: (1) cutaneous mycoses or tineas, especially if caused by *Microsporum, Trichophyton, Epidermophyton,* or *Mucutaneous candidiasis;* (2) mycolic keratitis, especially if caused by *Aspergillus, Fusarium,* or *Candida;* (3) amoebic keratitis, especially if caused by *Acanthamoeba;* (4) gastrointestinal disease, especially if caused by *Giardia lamblia, Entamoeba, Crytosporidium, Microsporidium,* or *Candida* (most commonly in immunocompromised animals); (5) urogenital infection, especially if caused by *Candida albicans* or *Trichomonas baginalis;* and (6) pulmonary disease, especially if caused by *Mycobacterium tuberculosis, Aspergillus,* of *Pneumocystis carinii.*

Other infectious diseases which are susceptible to treatment by the method of this invention are systemic infections of the animal. These include disseminated *Mycobacterium tuberculosis,* disseminated parasitic infections, such as *T. Gondii* and disseminated fungal infections, such as *Candida fungemia.*

B. Inhibition of the Fatty Acid Synthetic Pathway

Eukaryotic microbial cells which are dependent on their own endogenously synthesized fatty acid will express Type I FAS. This is shown both by the fact that FAS inhibitors are growth inhibitory and by the fact that exogenously added fatty acids can protect normal patient cells but not these microbial cells from FAS inhibitors. Therefore, agents which prevent synthesis of fatty acids by the cell may be used to treat infections. In eukaryotes, fatty acids are synthesized by Type I FAS using the substrates acetyl CoA, malonyl CoA and NADPH. Thus, other enzymes which can feed substrates into this pathway may also effect the rate of fatty acid synthesis and thus be important in microbes that depend on endogenously synthesized fatty acid. Inhibition of the expression or activity of any of these enzymes will effect growth of the microbial cells that are dependent upon endogenously synthesized fatty acid. In accordance with this invention, any suitable method for inhibiting fatty acid synthesis by microbial cells may be used to reduce infection in mammals. In addition, since the beta-ketoacyl synthase (condensing enzyme) is similar between Type I FAS and mycercosic acid synthase (MAS) it is anticipated that the inhibition of MAS may also reduce infection in mammals infected by organisms which express MAS, such as pathogenic mycobacterium.

The product of Type I FAS differs in various organisms. For example, in the fungi *S. cerevisiae* the products are predominately palmitate and sterate sterified to coenzyme-A. In *Mycobacterium smegmatis*, the products are saturated fatty acid CoA esters ranging in length from 16 to 24 carbons. These lipids are often further processed to fulfill the cells need for various lipid components. As used herein, the term (lipid biosynthesis) refers to any one of a combination of steps that occur in the synthesis of fatty acids or subsequent processing of fatty acids to make cellular components containing fatty acids. An example of this step is the mycoserosic acid synthase (MAS), which is present in pathogenic mycobacterium. This enzyme is responsible for the very long branched chain fatty acids seen in mycobacterium and Nocardia species.

Inhibition of key steps in down-stream processing or utilization of fatty acids may be expected to inhibit cell function, whether the cell depends on endogenous fatty acid or utilizes fatty acid supplied from outside the cell, and so inhibitors of these down-stream steps may not be sufficiently selective for microbial cells that depend on endogenous fatty acid. However, it has been discovered that administration of Type I fatty acid synthesis inhibitor to such microbes makes them more sensitive to inhibition by inhibitors of down-stream fatty acid processing and/or utilization. Because of this synergy, administration of a fatty acid synthesis inhibitor in combination with one or more inhibitors of down-stream steps in lipid biosynthesis and/or utilization will selectively affect microbial cells that depend on endogenously synthesized fatty acid. Preferred combinations include an inhibitor of FAS and acetyl CoA carboxylase, or FAS and an inhibitor of MAS.

C. Inhibitors Of Fatty Acid Synthesis

When it has been determined that a mammal is infected with cells of an organism which expresses Type I FAS, or if FAS has been found in a biological fluid from a patient, the mammal or patient may be treated according to the method of this invention by administering a fatty acid synthesis inhibitor. Inhibitors whose administration is within the contemplation of this invention may include any compound that shows demonstrable inhibition of lipid biosynthesis or utilization by a cell. Preferred inhibitors of fatty acid synthesis include the compounds listed in U.S. patent application Ser. No. 08/188,409, filed on even date herewith, entitled "Novel Compounds for Fatty Acid Synthesis Inhibition," incorporated herein by reference.

Any compound that inhibits fatty acid synthesis may be used to inhibit microbial cell growth, but of course, compounds administered to a patient must not be equally toxic to both patient and the target microbial cells. Preferred inhibitors for use in the method of this invention are those with high therapeutic indices (therapeutic index is the ratio of the concentration which affects patient cells to the concentration which affects the target microbial cells). Inhibitors with high therapeutic index can be identified in vitro by comparing the effect of the inhibitor on a human cell line, such as a normal fibroblast line, to the effect on susceptible microbial cells which have been shown to express high levels of FAS.

For example, therapeutic index may be determined by comparing growth inhibition of confluent normal fibroblasts to the dose of compounds resulting in the minimal inhibitory concentration for a given organism. The MIC for Cerulenin and wild type and multiply drug resistant strains of *M. tuberculosis* range from $\leq 1.5$ to 12.5 µg/ml. This drug dose can then be tested upon confluent cultures of normal human fibroblasts to determine a therapeutic index.

Breast cancer cells have been found to express fatty acid synthase, while most other tumor cells have not been tested for the presence or absence of this enzyme. Rochefort and co-workers have partially cloned FAS from breast cancer cells and found that FAS expression by breast cancer cell lines was correlated with responsiveness to progesterone (Chalbos, et al., *J. Biol. Chem.*, 262: 9923–9926, 1987). Based on this evidence, they concluded that cells expressing FAS were from tumors that were less de-differentiated and therefore less virulent (Chalbos, et al., *J, Nat'l. Cancer Inst.*, 82: 602–606. 1990). The present inventors have discovered that, contrary to the teaching of Rochefort, presence of OA-519, a protein which exhibits FAS activity, is highly correlated with the most virulent carcinomas.

Using standard in vitro growth inhibition assays, the inventors have demonstrated that inhibitors of OA-519 inhibit growth of carcinoma cells, but have little effect on Normal human fibroblasts. Indeed, fibroblasts, which have very low FAS activity, are resistant to FAS inhibitor concentrations that inhibit growth of more than 80% of breast carcinoma cells having high levels of OA-519 activity. Cells with the preferred level of fatty acid synthesis activity are easily obtained by the skilled worker, and examples of publicly available cell lines are provided: SKBR3, ZR-75-1, and MCF-7.

Inhibitors can be characterized by the concentration required to inhibit cell growth by 50% ($IC_{50}$ or $ID_{50}$). FAS inhibitors with high therapeutic index will, for example, be growth inhibitory to the carcimona cells at a lower concentration (as measured by $IC_{50}$) than the $IC_{50}$ for the non-malignant cells. Inhibitors whose effects on these two cell types show greater differences are more preferred. Preferred inhibitors of fatty acid synthesis will have $IC_{50}$ for cells with high fatty acid synthetic activity that is at least ½ log lower, more preferably at least 1 log lower, than the inhibitor's $IC_{50}$ determined for cells with low activity.

Lipid synthesis consists of multiple enzymatic steps. The data demonstrate that inhibition of lipid biosynthesis at two or more steps can create synergistic effects, lowering both the required concentration and the potential toxicity of any single agent. When microbes are treated by administration of a synergistic combination of at least one inhibitor of fatty acid synthesis and at least one inhibitor of either the enzymes which supply substrates to the fatty acid synthesis pathway or the enzymes that catalyze downstream processing and/or utilization of fatty acids, the therapeutic index will be sensitive to the concentrations of the component inhibitors of the combination. Optimization of the concentrations of the individual components by comparison of the effects of particular mixtures on human cell lines and susceptible cells is a routine matter for the skilled artisan. The dose of individual components needed to achieve the therapeutic effect can then be determined by standard pharmaceutical methods, taking into account the pharmacology of the individual components.

The inhibitor of fatty acid synthesis, or the synergistic combination of inhibitors will be administered at a level (based on dose and duration of therapy) below the level that would kill the animal being treated. Preferably, administration will be at a level that will not irreversibly injure vital organs, or will not lead to a permanent reduction in liver function, kidney function, cardiopulmonary function, gastrointestinal function, genitourinary function, integumentary function, musculoskeletal function, or neurologic function. On the other hand, administration of inhibitors at a level that kills some cells which will subsequently be regenerated (e.g., endometrial cells) is not necessarily excluded.

Acetyl CoA carboxylase and the condensing enzyme of the FAS and MAS complexes are likely candidates for inhibition. Fatty acid synthesis would be reduced or stopped by inhibitors of these enzymes. The result would be deprivation of membrane lipids, which would cause cell death. Normal human cells, however, would survive as they are able to import and use circulating lipid. Acetyl CoA carboxylase is the focal point for control of lipid biosynthesis. The condensing enzyme of the FAS complex is well characterized in terms of structure and function; the active center contains a critical cysteine thiol, which is the target of antilipidemic reagents, such as cerulenin. A wide variety of compounds have been shown to inhibit FAS, and selection of a suitable FAS inhibitor for treatment of carcinoma patients is within the skill of the ordinary worker in this art. FAS inhibitors can be identified by testing the ability of a compound to inhibit fatty acid synthase activity using purified enzyme. Fatty acid synthase activity can be measured spectrophotometrically based on the acetyl- or malonyl-CoA-dependent oxidation of NADPH, or radioactively by measuring the incorporation of radiolabeled acetyl- or malonyl-CoA. (Dils, et at, *Methods Enzymol,* 35: 74–83). Suitable FAS inhibitors may be selected, for example, from those exemplified in Table 1.

Table 1. Representative Inhibitors Of The Enzymes Of The Fatty Acid Synthesis Pathway
Inhibitors of Fatty Acid Synthase:
  1,3-dibromopropanone
  Ellman's reagent [5,5'-dithiobis(2-nitrobenzoic acid), DTNB]
  4-(4'-chlorobenzyloxy) benzyl nicotinate (KCD-232)
  4-(4'-chlorobenzyloxy) benzoic acid (MII)
  2[5(4-chlorphenyl)pentyl]oxirane-2-carboxylate (POCA) and its CoA derivative
  ethoxyformic anhydride
  thiolactomycin
  cerulenin
  phenylcerulenin
  melarsoprol
  iodoacetate
  phenylarsineoxide
  pentostam
  melittin
  methyl malonyl CoA
Inhibitors for citrate lyase:
  (−) hydroxycitrate
  (R,S)-S-(3,4-dicarboxy-3-hydroxy-3-methyl-butyl)-CoA
  S-carboxymethyl-CoA
Inhibitors for acetyl CoA carboxylase:
  sethoxydim
  haloxyfop and its CoA ester
  diclofop and its CoA ester
  clethodim
  alloxydim
  trifop
  clofibric acid
  2,4-D mecoprop
  dalapon
  2-alkyl glutarate
  2-tetradecanylglutarate (TDG)
  2-octylglutaric acid
  9-decenyl-1-pentenedioic acid
  decanyl-2-pentenedioic acid
  decanyl-1-pentenedioic acid
  (S)-ibuprofenyl-CoA
  (R)-ibuprofenyl-CoA
  fluazifop and its CoA ester
  clofop
  5-(tetradecycloxy)-2-furoic acid
  beta, beta'-tetramethylhexadecanedioic acid
  tralkoxydim
  free or monothioester of beta, beta prime-methyl-substituted hexadecanedioic acid (MEDICA 16)
  alpha-cyano-4-hydroxycinnamate
  S-(4-bromo-2,3-dioxobutyl)-CoA
  p-hydroxymercuribenzoate (PHMB)
  N6,O2-dibutyryl adenosine cyclic 3',5'-monophosphate
  N6,O2-dibutyryl adenosine cyclic 3',5'-monophosphate
  N2,O2-dibutyryl guanosine cyclic 3',5'-monophosphate
  CoA derivative of 5-(tetradecyloxy)-2-furoic acid (TOFA)
  2,3,7,8-tetrachlorodibenzo-p-dioxin
Inhibitors for malic enzyme:
  periodate-oxidized 3-aminopyridine adenine dinucleotide phosphate
  5,5'-dithiobis(2-nitrobenzoic acid)
  p-hydroxymercuribenzoate
  N-ethylmaleimide
  oxalyl thiol esters such as S-oxalylglutathione
  gossypol
  phenylglyoxal
  2,3-butanedione
  bromopyruvate
  pregnenolone The drug melarsoprol is a trivalent arsenical compound; Pentostam is a pentavalent antimony compound. Trivalent arsenicals react with adjacent thiol groups as do pentavalent antimonials. Fatty acid synthase activity requires multiple reduced thiol groups which would act as targets for inhibition by melarsoprol and other SH reagents.

Aside from these anti-parasite drugs, there are a host of other compounds which inhibit FAS at a variety of sites: protein kinase inhibitors block transcription of FAS in mammalian cells; colchicine interference with microtubules blocks insulin induction of FAS; melittin, a peptide from bee venom cross-links to the acyl carrier protein of FAS from some species; and cerulenin, an antibiotic, blocks the condensing enzyme activity of FAS. Cerulenin is a specific inhibitor of the condensing enzyme activity of fatty acid synthase as demonstrated by (Funabashi, et al *J. Biochem,* 105: 751–755, 1989) and cerulenin, formulated in liposomes or for non-invasive application as described below, is a preferred FAS inhibitor for the method of this invention.

Other preferred inhibitors of the condensing enzyme include a wide range of chemical compounds, including alkylating agents, oxidents, and reagents capable of undergoing disulphide interchange. The binding pocket of the enzyme prefers long chain, E, E, dienes such as:

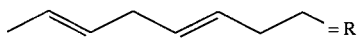 = R

In principal, a reagent containing the sidechain diene shown above and a group which exhibits reactivity with thiolate anions could be a good inhibitor of the condensing enzyme.

Cerulenin (2S) (3R) 2,3-epoxy-4-oxo-7,10 dodecadienoyl amide is an example:

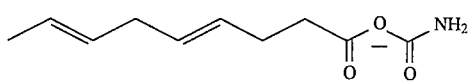

Examples of alternative compounds with different functional groups and the diene sidechain are shown below:

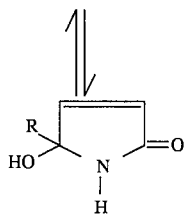

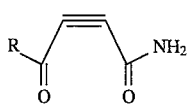

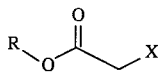

X = Tosyl, halide or other leaving group

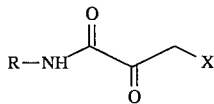

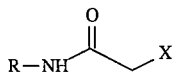

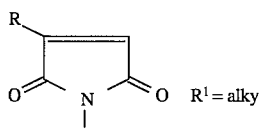   $R^1$ = alky

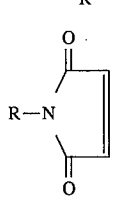

The R group tail can be varied according to the report of Morisaki, et. al. [*Eur. J. Biochem.* 211, 111 (1993)]. Increasing or decreasing the length of the sidechain reduces the inhibitory potency. Tetrahydrocerulenin is 80–150 times less potent than cerulenin. This result is consistent with the idea of π electrons in the side chain being of importance in bonding. Also, the trans double bonds confer conformational rigidity which may also be important.

In an alternative embodiment of this invention, septic patients are treated by administering compounds which inhibit either acetyl CoA carboxylase, malic enzyme or titrate lyase. Representative inhibitors of these enzymes are also shown in Table 1. The considerations for selection of the particular inhibitor are the same as discussed above for FAS inhibitors.

Assays for acetyl-CoA carboxylase are taught in U.S. Pat. No. 5,143,907, incorporated herein by reference, and these assays can be used by the skilled worker to determine the inhibitory constants for ACC inhibitors by well-known procedures.

Propanoates which inhibit acetyl CoA carboxylases from diverse organisms are preferred inhibitors. The inhibitors may be represented by the general structure shown below:

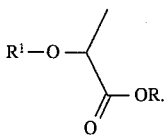

R can be hydrogen, alkyl, or aryl. The configuration at the asymmetric carbon atom can be R, S, or racemic.

The acetyl CoA carboxylase in plants is often more susceptible to the R isomer. $R^1$ is often aryl-oxy-aryl:

Ar—O—Ar—

The aromatic rings can be benzene, pyridine, etc. Halo- and other substituents on the aromatic rings are permissible. Examples of propanoates are shown below and/or listed in Table 1:

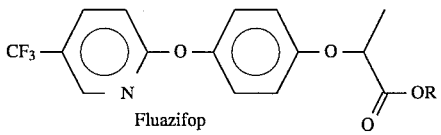
Fluazifop

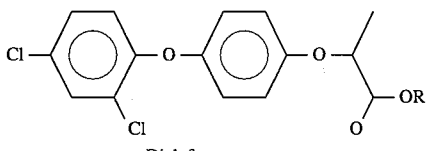
Diclofop

Dichlorprop

Some homologs of propanoates are good inhibitors. An example is TOFA, 5 (tetradecyloxy)-2-furoic acid, a potent acetyl CoA carboxylase inhibitor. The structure is shown below:

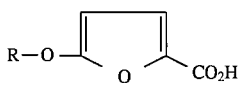

C-2 in this case is not chiral. The R group is a linear saturated 14-carbon sidechain. Methods of synthesizing this compound and related compounds that are also contemplated by this invention are taught in U.S. Pat. No. 4,146,623, incorporated herein by reference.

Another example of a homolog of the propanoates is TDGA or tetradecylglycidic acid:

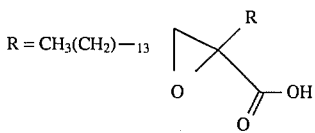

R = CH₃(CH₂)—₁₃

Hydrophobic character and a carboxyl carbon beta to an ether oxygen are common structural traits. Other relevant 2-substituted propanoates include compounds such as ibuprofen, ibuproxam and derivatives thereof.

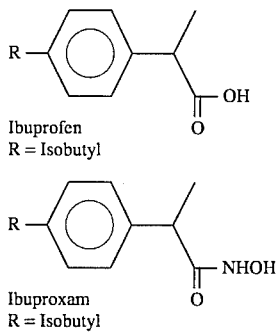

Ibuprofen
R = Isobutyl

Ibuproxam
R = Isobutyl

Ketocylohexenes represent another class of acetyl CoA carboxylase inhibitors. One example is sethoxydim:

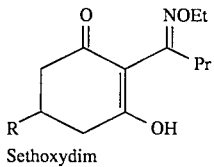

Sethoxydim

Where R is an ethylthiopropyl group.

Another class of compounds which inhibit acetyl CoA carboxylases is represented by the general structure:

CO₂H
|
R
|
CO₂H

Specific examples such as glutaric acid and pentenedioic acids are listed in Table 1.

In addition to acetyl CoA carboxylase and FAS, other target enzymes include citrate lyase and malic enzyme. These enzymes provide acetate and NADPH for lipid biosynthesis via FAS. The respective reactions are as follows:

Citrate + ATP + CoA ⟶ Ac—CoA + ADP + Oxaloacetate

Citrate lyase

Malate + NADP ⟶ Pyruvate + CO₂ + NADPH

Malic Enzyme

Therapeutic compounds could also be based on these inhibitors as the deprivation of acetyl CoA or NADH would also stop the lipid synthesis.

Of the enzymes in the fatty acid synthetic pathway, FAS is the preferred target for inhibition because it acts only within the pathway to fatty acids, while the other three enzymes are implicated in other cellular functions. Therefore, inhibition of one of the other three enzymes is more likely to affect normal human cells. However, where an inhibitor for one of these enzymes can be shown to have a high therapeutic index as described above, the inhibitor may be used therapeutically according to this invention. The skilled clinician will be able to select a method of administration and to administer inhibitors of any enzyme in the synthetic pathway for fatty acids to treat infected patients identified above, based on the teaching below.

This invention does not contemplate the use of inhibitors that are generally inhibitory to a large number of different cellular enzyme systems and pathways, such as the phosphite-boranes disclosed in U.S. Pat. No. 5,143,907, or iodoacetamide unless the particular inhibitor can be made relatively specific for lipid biosynthesis as shown by a high therapeutic index (for example, as pan of a synergistic combination discussed above).

The elongation and oxidation of fatty acids may be critical for production of necessary membrane lipids. For that purpose, the elongation and oxidation steps and any other processing steps for fatty acids would be likely molecular targets for therapeutics. For example. *M. tuberculosis* elongates fatty acid using MAS; thus MAS is also a preferred target.

D. Administration of Inhibitors of Fatty Acid Synthesis

Inhibitors of fatty acid synthesis are preferably formulated in pharmaceutical compositions containing the inhibitor and a pharmaceutically acceptable carrier. The pharmaceutical composition may contain other components so long as the other components do not reduce the effectiveness of the synthesis inhibitor so much that the therapy is negated. Pharmaceutically acceptable carriers are well known, and one skilled in the pharmaceutical art can easily select carriers suitable for particular routes of administration (*Remington's Pharmaceutical Sciences,* Mack Publishing Co., Easton, Pa., 1985). The pharmaceutical compositions containing any of the inhibitors of this invention may be administered by parenteral (subcutaneously, intramuscularly, intravenously, intraperitoneally, intrapleurally, intravesicularly or intrathecally), topical, oral, rectal, or nasal route, as necessitated by choice of drug, type of infection, etc.

The concentrations of the active agent in pharmaceutically acceptable carriers may range from 0.1 μg/ml to 100 μg/ml. The dose used in a particular formulation or application will be determined by the requirements of the particular type of infection and the constraints imposed by the characteristics and capacities of the carrier materials.

Dose and duration of therapy will depend on a variety of factors, including the therapeutic index of the drugs, type of infection, patient age, patient weight, and tolerance of toxicity. Dose will generally be chosen to achieve serum concentrations from about 0.1 μg/ml to about 100 μg/ml. Preferably, initial dose levels will be selected based on their ability to achieve ambient concentrations shown to be effective against the target organism in-vitro, such as the model system used to determine therapeutic index, and in-vivo models and in clinical trials, up to maximum tolerated levels. Most preferably, antimicrobial therapy will be tailored to the individual patient and the circulatory concentration of the antimicrobial agent be monitored regularly. The dose of a particular drug and duration of therapy for a particular patient can be determined by the skilled clinician using standard pharmacological approaches in view of the above factors. The response to treatment may be monitored by analysis of blood or body fluids for culture of the organism, antigen detection, direct nucleic acid hybridization testing such as PCR, or microscopic detection of organisms in tissue biopsies or body fluids. The skilled clinician will adjust the dose or duration of therapy based on the response to treatment revealed by these measurements.

In a preferred mode, the inhibitor of fatty acid synthesis is formulated in a pharmaceutical composition and applied to an externally accessible surface of the infected animal. Diseases which cause lesions in externally accessible surfaces may be treated by non-invasive administration of an inhibitor of fatty acid synthesis. Non-invasive administration includes (1) topical application to the skin in a formulation, such as an ointment or cream, which will retain the inhibitor in a localized area; (2) oral administration; (3) nasal administration as an aerosol; (4) intravaginal application of the inhibitor formulated in a suppository, cream or foam; (5) rectal administration via suppository, irrigation or other suitable means; (6) bladder irrigation; and (7) administration of aerosolized formulation of the inhibitor to the lung. Aerosolization may be accomplished by well known means, such as the means described in International Patent Publication WO 93/12756, pages 30–32, incorporated herein by reference.

A preferred strategy is to administer these compounds locally or topically in gels, ointments, solutions, impregnated bandages, liposomes, or biodegradable microcapsules. Compositions or dosage forms for topical application may include solutions, lotions, ointments, creams, gels, suppositories, sprays, aerosols, suspensions, dusting powder, impregnated bandages and dressings, liposomes, biodegradable polymers, and artificial skin. Typical pharmaceutical carriers which make up the foregoing compositions include alginates, carboxymethylcellulose, methylcellulose, agarose, pectins, gelatins, collagen, vegetable oils, mineral oils, stearic acid, stearyl alcohol, petrolatum, polyethylene glycol, polysorbate, polylactate, polyglycolate, polyanhydrides, phospholipids, polyvinylpyrrolidone, and the like.

A particularly preferred formulation for fatty acid synthesis inhibitors is in liposomes. Liposomes containing fatty acid synthesis inhibitors according to this invention may be prepared by any of the methods known in the art for preparation of liposomes containing small molecule inclusions. Liposomes that are particularly suited for aerosol application to the lungs are described in International Patent Publication WO 93/12756, pages 25–29, incorporated herein by reference.

The compositions described above may be combined or used together or in coordination with another antibiotic, antifungal or antiviral substance.

E. Selective Chemotherapeutic Method

In a preferred embodiment, the method of this invention also protects normal cells of patients treated with fatty acid synthesis inhibitors. To protect normal animal tissues such as liver (which express normally low ranges of fatty acid synthase activity) from potential toxicity, the level of FAS enzyme and/or fatty acid synthetic activity may be down-regulated before and/or during therapy. Down regulation may be accomplished by supplying essential fatty acids in the diet, by reduction of caloric intake or by other effective methods, such as administration of glucagon.

Because FAS is an inducible enzyme in normal animal tissues, reduction in caloric intake will result in lower expression of FAS by patient cells. The susceptible microbial cells usually express FAS constitutively. In a patient with limited caloric intake, FAS expression is limited to microbial cells, and the cytotoxic effect of FAS inhibitors will be similarly limited. Down-regulation of FAS expression is usually coupled to fatty acid synthesis inhibitor therapy by reducing caloric intake of the patient before and during administration of the inhibitor.

Another suitable method of reducing FAS expression is exogenous administration of fatty acids, preferably, essential fatty acids. These fatty acids may be formulated in any way that results in the down-regulating FAS expression of patient cells. This could be by including them in the diet of the patient or by formulating them in the same pharmaceutical composition as the fatty acid synthesis inhibitor, or any other suitable method.

Diets suitable for reducing FAS expression in patient tissue are easily within the skill of the ordinary clinician. Any method of reducing FAS expression by patient cells is within the contemplation of the method of this invention, as long as the FAS level in patient cells is reduced during the time that the fatty acid synthesis inhibitor is present in the patient at levels that would be cytotoxic to susceptible microbial cells.

EXAMPLES

The following Examples are provided for purposes of illustration only. They are not intended to limit the invention described above, which is only limited by the appended claims.

Example 1

Susceptibility of *M. tuberculosis*

Drug susceptibility or resistance is determined by the modified version of the conventional proportion method. The critical proportion for resistance is taken as 1% for all anti-tuberculosis drugs. Resistance is determined through comparison of the growth rate in control vials containing a 1% inoculum and broth vials containing the specific test drug. This method has been found comparable to the conventional proportional method or the resistance ratio method. Similarly accuracy and reproducibility of this method have yielded excellent results.

Determination of the activity of cerulenin against *M. tuberculosis* was performed utilizing a commercially available radiometric system which is based on the same principle that is utilized in conventional antibiotic susceptibility testing of *M. tuberculosis*. The significant difference from the conventional methods is that a liquid medium is used and rather than counting colonies after approximately 3 weeks of incubation, the growth is monitored through measurement of metabolism of $^{14}C$-labeled palmitic acid to $^{14}CO_2$ radiometrically with the results being available in 3 to 5 days.

Organisms:

A control organism *M. tuberculosis* H37RV was used throughout the studies. Due to the relatively slow growth rate of *M. tuberculosis* H37RV, *Candida albicans* strain known to be susceptible to cerulenin was used to control antibiotic concentration as well as *M. tuberculosis* H37RV. The remaining isolates of *M. tuberculosis* were clinical isolates from this institution or referred here as part of a cooperate susceptibility study on strains of *M. tuberculosis* obtained from patients seen in Haiti.

Susceptibility Test Method For Mycobacteria

Susceptibility testing was performed using a commercially available Middlebrook 7H12 broth media containing $^{14}C$-labeled palmitate as an indicator substrate. Growth in this system is determined through measurement of $^{14}CO_2$ generation. A 1 mg/ml initial stock solution of cerulenin was prepared and diluted to the following concentrations (μg/ml): 1000, 500, 250, 125, 62.5. A 0.1 ml of the stock concentrations were then added to individual 4.0 ml Bactec bottles resulting in the following final concentrations (μg/ml): 25, 12.5, 6.25, 3.0, 1.5. For each strain tested 0.1 ml of organism was added to each bottle at each concentration tested, a direct control (bottle containing diluent, DMSO, but no antibiotic, and a 1:100 organism dilution which is also added to broth bottle not containing antibiotic. All broth bottles were incubated at 35° C. and read daily from Growth Index (GI proportional to quantity of $^{14}CO_2$ generated) readings. Results were recorded until the GI of the 1:100 control reached 30. At this time, the minimum inhibitory concentration of the isolate was determined. Control organisms for each susceptibility run included *Candida albicans* (cerulenin MIC ≦1.5 μg/ml). A 0.5 McFarland suspension of *C. albicans* is prepared and 0.1 ml of this suspension was added to each concentration of cerulenin in the 12B Bactec bottles.

The minimum inhibitory concentration of each isolate was determined using the following criteria. Once the growth index (GI) of the 1:100 control bottle had reached a value of 30, the change (Δ) in growth index for a one day period was calculated as well as the growth index change (Δ) at each concentration tested during the same 24 hour period. The MIC was defined as the lowest cerulenin concentration that yielded a growth index change less than that of the 1:100 control bottle.

Results

Tables 2 and 3 show representative results of susceptibility testing of susceptible (H37RV) and multiply drug (H389) resistant isolates of *M. tuberculosis*. Table 4 shows the susceptibility results of isolates recovered from Haitian patients using the same methodology, against primary and secondary drugs used currently in the treatment of *M. tuberculosis*. As can be seen cerulenin, in this susceptibility test system, does have inhibitory activity against both susceptible and multiply drug resistant. *M. tuberculosis* with minimum inhibitory concentrations ranging from <1.5 μg/ml to 6.25 μg/ml.

Example 2

Toxoplasma Suspectibility Testing

Cerulenin activity against *T. gondii* was determined using a tissue culture system. Tachyzoites of *T. gondii* were grown in human lung fibroblast (MRC-5 cell line) to a concentration of $-10^7$ organisms/mi. Susceptibility testing was performed in 24 well tissue culture plates containing human foreskin fibroblast (ATCC Hs68 cell line) and serially diluted concentrations of cerulenin and appropriate control wells. The minimum inhibitory concentration of *T. gondii* was determined as the well containing the lowest concentration of cerulenin in which no growth of *T. gondii* occurred following 72 hours of incubation.

Organisms

The *Toxoplasma gondii* RH strain was used in all experiments. *T. gondii* RH tachyzoites were maintained frozen at −70° C and through serial passage on MRC-5 cells.

Susceptibility Test Method

The *T. gondii* RF tachyzoites were grown in human lung fibroblast (MRC-5) in 16×150 mm screw-capped tubes in minimal essential medium (MEM) (Whittaker) supplemented with 100 μ/ml penicillin, 0.01% glutamine, 50 μg/ml gentamicin, 0.01% Hepes buffer and 0.02% fetal calf serum. After visual lysis (3–4 days), supernatants containing $-10^7$ tachyzoites were collected and used as inoculum for susceptibility testing. Tests were performed in 24 well tissue culture plates containing human foreskin fibroblast (ATCC Hs68) in supplemented MEM. Cerulenin (1 mg) was dissolved initially in DMSO and subsequently diluated in sterile water to yield concentrations of 100 μg/ml, 50 μg/ml, 25 μg/ml, and 12.5 μg/ml. For testing 100 μl of each cerulenin concentration was added to a separate tissue culture well containing 0.8 ml of supplemental MEM plus 100 of *T. gondii* tachyzoites (~$10^6$ organisms) grown as described previously for a final volume of 1 ml. Control wells, one containing no cerulenin and one containing 10% DMSO-water (100 μl), were included in each test series. All susceptibility tests were performed in quadruplicate. Test panels were incubated at 37C and examined daily for toxicity, fibroblast lysis, and growth of *T. gondii*.

Results

Repeated testing of *T. gondii* in the outlined fibroblast susceptibility system demonstrated consistent inhibition of *T. gondii* tachyzoite growth in tissue culture wells containing 2.5 μg/ml of cerulenin.

We claim:

1. A method of inhibiting growth of invasive microbial cells selected from the group consisting of *Mycobacterium tuberculosis*, multiply-drug resistant *M. tuberculosis* and *Toxoplasma sp.* in an animal, said cells being dependent on endogenously synthesized fatty acid, comprising administering an inhibitor of fatty acid synthesis to the microbial cells in an amount sufficient to inhibit growth of said cells, wherein said inhibitor is an inhibitor of the enzyme fatty acid synthase having $IC_{50}$ for growth of said cells which is at least 1 log lower that $IC_{50}$ for growth of normal human fibroblasts.

2. The method according to claim 1 wherein the administration is substantially non-systemic.

3. A method according to claim 2, wherein said inhibitor of fatty acid synthesis is formulated in a pharmaceutical composition suitable for topical application.

4. A method according to any of claims 2 and 3, wherein said inhibitor of fatty acid synthesis is formulated in liposomes.

5. The method according to any of claims 2 and 3, wherein the inhibitor is cerulenin.

6. The method according to claim 4, wherein the inhibitor is cerulenin.

7. A method according to claim 1, further comprising the step of reducing fatty acid synthase expression of patient tissue.

8. A method according to claim 7, wherein the step of reducing fatty acid synthase expression comprises reducing the caloric intake of said patient.

9. A method according to claim 7, wherein the step of reducing fatty acid synthase expression comprises administering a composition containing long chain free fatty acid or acyl glyceride to said patient.

10. A method according to claim 9, wherein the composition containing long chain free fatty acid or acyl glyceride supplies essential fatty acids to said patient.

11. The method according to claims 1, 2 and 3 wherein the inhibitor of fatty acid synthesis exhibits a $K_i$ for inhibition of fatty acid synthesis of less than 10 μM.

12. The method according to claims 1, 2 and 3 wherein the inhibitor is cerulenin.

13. The method according to claim 1, further wherein an inhibitor of lipid biosynthesis is co-administered with the inhibitor of fatty acid synthesis.

14. The method according to any one of claims 1, 2, 6, 11, 12 or 13, wherein the microbial cells are *Toxoplasma sp.*

* * * * *

UNITED STATES PATENT AND TRADEMARK OFFICE
CERTIFICATE OF CORRECTION

PATENT NO. : 5,614,551
DATED : March 25, 1997
INVENTOR(S) : DICK, et al.

It is certified that error appears in the above-indentified patent and that said Letters Patent is hereby corrected as shown below:

In claim 1, column 16, line 29, after "lower", insert --than--, and delete "that".

In claim 14, column 16, line 64, after claims 1,", insert --2-6--, and delete "2, 6".

Signed and Sealed this

Tenth Day of February, 1998

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,614,551
DATED : March 25, 1997
INVENTOR(S) : DICK, et al.

It is certified that error appears in the above-indentified patent and that said Letters Patent is hereby corrected as shown below:

Column 16, line 18, after the paragraph ending with "cerulenin":
Append Tables 2, 3, and 4, attached hereto.

Signed and Sealed this

Seventh Day of July, 1998

*Attest:*

BRUCE LEHMAN

*Attesting Officer*     *Commissioner of Patents and Trademarks*

TABLE 2

Susceptibility of *M. tuberculosis* to Cerulenin

<u>Growth Index Reading</u>

| Organism | Cerulenin Concentration | DAY | | | | | | | | | | MIC (µg/ml) |
|---|---|---|---|---|---|---|---|---|---|---|---|---|
| H155 | | 1 | 2 | 3 | 4 | 5 | 6 | 7 | 8 | 9 | 10 | |
| Control 1:100 | 0 | 1 | 7 | 18 | 39 | 95 | | | | | | |
| | 1.5 | 167 | 597 | 721 | 657 | 611 | | | | | | |
| | 3.0 | 143 | 481 | 603 | 559 | 475 | | | | | | |
| | 6.25 | 151 | 525 | 693 | 660 | 539 | | | | | | ≤1.5 |
| | 12.5 | 144 | 483 | 668 | 658 | 597 | | | | | | |
| | 25 | 102 | 381 | 578 | 617 | 643 | | | | | | |
| *C. albicans* | | 1 | 2 | 3 | 4 | 5 | 6 | 7 | 8 | 9 | 10 | |
| Control 1:100 | 0 | 0 | 12 | 55 | 143 | 182 | 178 | | | | | |
| | 1.5 | 0 | 0 | 0 | 0 | 0 | 0 | | | | | |
| | 3.0 | 0 | 0 | 0 | 0 | 0 | 0 | | | | | |
| | 6.25 | 1 | 0 | 0 | 0 | 0 | 0 | | | | | ≤1.5 |
| | 12.5 | 0 | 0 | 0 | 0 | 0 | 0 | | | | | |
| | 25 | 0 | 0 | 0 | 0 | 0 | 0 | | | | | |
| H37RV | | 1 | 2 | 3 | 4 | 5 | 6 | 7 | 8 | 9 | 10 | |
| Control 1:100 | 0 | 1 | 0 | 0 | 0 | 0 | 2 | 7 | 15 | 32 | 63 | |
| | 1.5 | 8 | 24 | 26 | 27 | 35 | 40 | 57 | 89 | 150 | 26<br>5 | |
| | 3.0 | 6 | 18 | 21 | 21 | 23 | 25 | 30 | 39 | 52 | 81 | 3 |
| | 6.25 | 6 | 20 | 26 | 25 | 26 | 26 | 28 | 31 | 37 | 45 | |
| | 12.5 | 8 | 28 | 32 | 21 | 32 | 31 | 33 | 34 | 39 | 44 | |
| | 25 | 5 | 28 | 32 | 21 | 32 | 31 | 33 | 34 | 39 | 43 | |

TABLE 3

Susceptibility of *M. tuberculosis* to Cerulenin

Growth Index Reading

| Organism | Cerulenin Concentration | DAY | | | | | | | | | | MIC * (µg/ml) |
|---|---|---|---|---|---|---|---|---|---|---|---|---|
| 8H31 | | 1 | 2 | 3 | 4 | 5 | 6 | 7 | 8 | 9 | 10 | |
| Control 1:100 | 0 | 3 | 8 | 20 | 54 | 130 | 223 | 439 | 758 | 999 | | 3 |
| | 1.5 | 284 | 479 | 437 | 514 | 703 | 707 | 999 | 999 | 999 | | |
| | 3.0 | 249 | 434 | 417 | 448 | 554 | 517 | 676 | 905 | 999 | | |
| | 6.25 | 246 | 464 | 437 | 454 | 503 | 431 | 547 | 707 | 948 | | |
| | 12.5 | 216 | 449 | 442 | 439 | 477 | 440 | 468 | 542 | 655 | | |
| | 25 | 146 | 367 | 487 | 511 | 563 | 505 | 536 | 569 | 664 | | |
| 2H339 | | 1 | 2 | 3 | 4 | 5 | 6 | 7 | 8 | 9 | 10 | |
| Control 1:100 | 0 | 5 | 15 | 65 | 75 | 456 | 215 | 429 | 716 | 999 | | 3 |
| | 1.5 | 420 | 730 | 746 | 855 | 999 | 876 | 950 | 906 | 774 | | |
| | 3.0 | 369 | 642 | 626 | 622 | 694 | 943 | 726 | 815 | 903 | | |
| | 6.25 | 331 | 591 | 572 | 544 | 624 | 534 | 588 | 680 | 744 | | |
| | 12.5 | 291 | 577 | 603 | 550 | 592 | 490 | 525 | 590 | 725 | | |
| | 25 | 143 | 452 | 622 | 671 | 650 | 525 | 529 | 545 | 615 | | |
| H389 | | 1 | 2 | 3 | 4 | 5 | 6 | 7 | 8 | 9 | 10 | |
| Control 1:100 | 0 | 4 | 13 | 36 | 82 | 193 | 291 | 568 | 912 | 999 | | 3 |
| | 1.5 | 154 | 338 | 371 | 437 | 629 | 661 | 986 | 999 | 999 | | |
| | 3.0 | 166 | 368 | 375 | 381 | 494 | 479 | 665 | 954 | 999 | | |
| | 6.25 | 141 | 311 | 303 | 322 | 377 | 347 | 439 | 607 | 869 | | |
| | 12.5 | 167 | 441 | 457 | 460 | 505 | 441 | 502 | 588 | 761 | | |
| | 25 | 86 | 302 | 409 | 452 | 532 | 478 | 539 | 617 | 745 | | |

TABLE 4

***Mycobacterium tuberculosis* susceptibility to cerulenin and other antituberculosis antibiotics**

| *M. tuberculosis* Isolate | INH 0.1 0.1µg/ml | INH 0.4 0.4 µg/ml | STREP 2 µg/ml | ETH 2.5 µg/ml | RIF 2 µg/ml | PZA 100 µg/ml | CER 6.25 µg/ml |
|---|---|---|---|---|---|---|---|
| H37RV | S | S | S | S | S | S | S |
| 8H31 | R | R | S | S | R | S | S |
| 2H339 | S | S | R | S | S | S | S |
| Morgan JH1 | S | S | S | S | S | | S |
| Monkey JH2 | S | S | S | S | S | | S |
| H389 | R | R | R | R | R | R | S |
| H433 | R | R | S | S | S | S | S |
| H441 | | | | | | S | S |
| H039.5 | | | | | | | S |
| 6H32 | R | R | S | R | S | | S |
| H155 | R | | S | S | S | | S |

S = Susceptible
R = Resistant